United States Patent [19]
Zambito et al.

[11] 3,987,046
[45] Oct. 19, 1976

[54] PROCESS FOR EXTRACTING AND PURIFYING 3,6-BIS-(5-CHLORO-2-PIPERIDINYL)-2,5-PIPERAZINE DIONE

[75] Inventors: Arthur J. Zambito, Rahway; Paul Davis, Metuchen, both of N.J.

[73] Assignee: Merck & Co., Inc., Rahway, N.J.

[22] Filed: Dec. 11, 1975

[21] Appl. No.: 639,726

Related U.S. Application Data

[63] Continuation of Ser. No. 478,550, June 11, 1974, abandoned.

[52] U.S. Cl. .......................... 260/268 DK; 424/250
[51] Int. Cl.$^2$ ...................................... C07D 401/14
[58] Field of Search ............................. 260/268 DK

[56] References Cited
UNITED STATES PATENTS

3,718,651   2/1973   Gitterman et al. ........... 260/268 DK

*Primary Examiner*—Nicholas S. Rizzo
*Assistant Examiner*—Jose Tovar
*Attorney, Agent, or Firm*—David L. Rose; Walter Patton; J. Jerome Behan

[57] ABSTRACT

This invention relates to the process for the purification of 3,6-bis(5-chloro-2-piperidinyl)-2,5-piperazinedione dihydrochloride, also known as Compound 593A, obtained as the free base from the fermentation broth of a strain of *Streptomyces griseoluteus* designated as NRRL 3412 by adsorbtion of the compound on a resin comprising a nonionic macro porous copolymer of styrene cross-linked with divinylbenzene. The resin is eluted with an organic aqueous dilute mineral acid solvent mixture in which the adsorbed compound is soluble. The compound is extracted from the eluate and further purified by fractional crystallization.

3 Claims, No Drawings

PROCESS FOR EXTRACTING AND PURIFYING 3,6-BIS-(5-CHLORO-2-PIPERIDINYL)-2,5-PIPERAZINE DIONE

This is a continuation of application Ser. No. 478,550 filed, June 11, 1974, now abandoned.

BACKGROUND OF THE INVENTION

The discovery that effective therapeutic agents could be obtained as products resulting from bacterial fermentation has immeasurably increased the armamentarium necessary to maintain the healthy state or to reverse the diseased state. As witness to this is the discovery of penicillin, streptomycin, and also certain anti-tumor agents resulting from microbial fermentation.

Compound 593A is an antibacterial and anti-tumor agent first discovered by Dr. C. O. Gitterman et al. and described in U.S. Pat. No. 3,718,651. The free base of Compound 593A is produced by fermentation of *Streptomyces griseoluteus* NRRL 3412. Gitterman et al. have described the production, recovery, and characterization of Compound 593A. This patent discloses a procedure which involves extraction of the compound with wet-butanol from concentrated fermentation broth followed by concentration.

The essential features of the present process is the direct absorption of Compound 593A free base on a surface active agent from whole, filtered broth; elution of the compound and further purification by fractional crystallization at controlled pH. The process of this invention affords the isolation of Compound 593A free base in high yield from fermentation broth and permits a facile separation of closely related impurities to give a highly purified product.

SUMMARY OF THE INVENTION

This invention relates to a method of obtaining from fermentation broth substantially pure 3,6-bis(5-chloro-2-piperidinyl)-2,5-piperazinedione, hereinafter also called Compound 593A free base, having the structural formula:

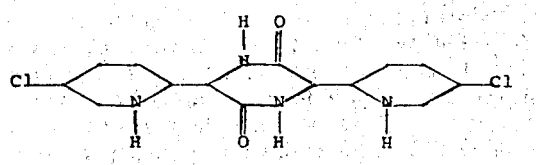

It is produced by growing a strain of *Streptomyces griseoluteus* in suitable fermentation media.

It is the object of this invention to provide a method for recovering this substance from fermentation broths. Other objects will be apparent from the detailed description hereinafter provided.

In the method of this invention the whole fermentation broth is filtered and the filtrate containing the Compound 593A free base is passed through a column packed with a surface active agent. Suitable surface active agents for adsorbing Compound 593A free base are activated charcoal, silica gel or basic aluminum oxide, cation or anion exchange resins, or neutral adsorbing resins. The adsorbed Compound 593A free base is eluted with a suitable solvent. In the case of activated charcoal, it is eluted with a polar organic solvent or with dilute mineral acid; in the case of silica gel, with methanol-chloroform; n-butanol-H$_2$O or n-butanol-H$_2$O-acetic acid preferably in the ratio 65:25:10. In the case of a cation exchange resin, for example, sulfonated copolymer of styrene cross-linked with divinylbenzene (a suitable resin is known by the tradename Dowex 50W) the adsorbed Compound 593A free base is eluted with 4N-HCl. A suitable anion exchange resin is a polystyrene quaternary ammonium anion exchange resin (a suitable resin is known by the Rohm and Haas tradename of Amberlite IRA-400). In the case of neutral adsorbing resins, for example, hydrophobic non-ionic macro porous copolymers of polystyrene cross-linked with divinylbenzene known by the tradenames Amberlite XAD-1 to XAD-12, suitable solvents for eluting adsorbed Compound 593A free base are water, lower-alkanols or solutions of the two, e.g. methanol, ethanol isopropanol, butanol, and the like or methanol-water (1:1), butanol-water; lower-alkanols and chlorinated solvents, e.g. methanol-chloroform; solutions of lower-alkanones with water or dilute mineral acid, e.g. acetone-water (1:1) or acetone 0.1N HCl. The preferred solvent for eluting Compound 593A from XAD-2 resin is acetone-0.1N HCl (1:1).

After the adsorbed Compound 593A free base is eluted with a suitable solvent the eluate is concentrated to a small volume and the antibiotic extracted into a water immiscible polar organic solvent. Suitable extraction solvents are lower-alkyl esters of lower alkanoic acids e.g. methyl acetate, ethyl acetate, propyl acetate, butyl acetate, and the like; water immiscible lower molecular weight alcohols, e.g. wet butanol or benzyl alcohol. Chlorinated solvents such as chloroform may also be used. Water miscible extraction solvents may be used if the eluate is first concentrated to near dryness or if it is first saturated with salt. Under these conditions suitable extraction solvents are lower-alkanols e.g. methanol, ethanol, n-propanol, isopropanol or lower-alkanones, e.g. acetone, methylethyl ketone and the like.

In the preferred method of this invention the whole fermentation broth is acidified and filtered and the filtrate, after adjusting the pH to basic, is passed through a column packed with the neutral adsorbing resin XAD-2 to adsorb the Compound 593A free base from the filtered broth. The adsorbed compound is eluted with a solution of acetone and hydrochloric acid and the eluate concentrated and the antibiotic extracted into the polar organic solvent ethyl acetate. The solid obtained from the concentrated extract is washed with a non-polar organic solvent and further purified by fractional crystallization from aqueous acid solutions under controlled pH conditions. The fractional crystallization is carried out by dissolving the antibiotic in pH 2.5 water, decolorizing with charcoal, and adjusting the pH slowly to about 5 by dropwise addition of sodium hydroxide solution and filtering off the crystallized solid.

DESCRIPTION OF THE PREFERRED EMBODIMENTS 3,6-bis(5-chloro-2-piperidinyl)-2,5-piperazinedione is formed by growing under controlled conditions a previously known strain of *Streptomyces griseoluteus*. The original microorganism which was isolated from soil collected in the geographical area of Richmond, Union of South Africa, has been designated as MA-1241 in the culture collection of MERCK & CO., Inc., Rahway, N.J. The parent culture, MA-1241, has also been deposited in the culture collection of the Northern Utilization Research and Development Branch of the U.S. Department of Agriculture at Peoria, Ill., where it is available to the public without restriction as NRRL 3412.

Complete taxonomy and morphology studies of *Streptomyces griseoluteus* are reported in U.S. Pat. No. 3,718,651. Based on taxonomic studies *Streptomyces griseoluteus* was identified as an actinomycete. It was found to belong to the genus *Streptomyces* and it was found that the parent culture closely resembles *Streptomyces griseoluteus* and *Streptomyces aureofaciens*. On comparison with the two most closely related microorganisms the specie designation *Streptomyces griseoluteus* was assigned to NRRL 3412.

*Streptomyces griseoluteus* is simply illustrative of the type of strain of microorganism which can be used in the production of Compound 593A free base and it should be understood that the present invention is not limited to organisms meeting these particular descriptions. This invention includes the use of the other microorganisms, including strains of actinomycetes either isolated from nature or obtained by mutation as, for example, those obtained by natural selection or those produced by mutating agents, for example, X-ray irradiation, ultraviolet irradiation, nitrogen mustards and the like which, under suitable conditions will yield Compound 593A free base.

The product of this invention may be produced by either surface or submerged cultures; however, it is presently preferred to carry out the fermentation in the submerged state. Small scale fermentation batches may be conveniently prepared by placing suitable quantities of nutrient medium in flasks, sterilizing the flasks and contents by heating to about 120° C. for 20 minutes, cooling and inoculating the flasks with vegetative cultures of a 3,6-bis(5-chloro-2-piperidinyl)-2,5-piperazinedione producing strain of *Streptomyces griseoluteus*, loosely sealing the flasks with cotton and allowing fermentation to proceed on a shaker in a constant temperature room at 28° C. for 3–5 days. Larger fermentation batches may be prepared, using suitably sized tanks provided with an agitator and a means of aerating the fermentation medium. In this method the medium and tanks containing the sterilized medium is inoculated with a vegetative culture. The fermentation is allowed to proceed from 2–4 days with constant agitation or aeration of the nutrient medium at a constant temperature of about 28° C. In carrying out the fermentation according to this process it may be desirable to add a small amount of a suitable anti-forming agent. Suitable agents may include soybean oil, castor oil, 1% octadecanol in mineral oil, or a polymerized propylene glycol such as polyglycol 2,000. These agents will thus control any excess foaming that may occur in the fermentation broth during fermentation.

Aqueous media, such as those employed for the production of antibiotics, are suitable for producing 3,6-bis(5-chloro-2-piperidinyl)-2,5-piperazinedione. Such media contain sources of carbon and nitrogen assimilable by the microorganism and inorganic salts. In addition, the fermentation media contain traces of metals necessary for the growth of the microorganism which are commonly supplied as impurities incidental to the addition of other constituents of the medium.

In general, carbohydrates such as sugars, for example, glucose, maltose, fructose, and the like, and starches such as grains, for example, oats and rye, corn starch, corn meal, and the like, can be used either alone or in combination as sources of assimilable carbon in the nutrient medium. The exact quantity of the carbohydrate source or sources utilized in the medium will depend in part upon the other ingredients of the medium, but it is usually found that an amount of carbohydrate between about 1 and 6% by weight of the medium is satisfactory. These carbon sources can be used individually or several such carbon sources may be combined in the medium.

Satisfactory nitrogen sources include myriad proteinaceous materials such as various forms of hydrolysates of casein, soybean meal, corn steep liquor, distilled solubles, yeast hydrolysates, and the like. The various sources of nitrogen, either alone or in combination, are used in amounts ranging from about 0.2–6% by weight of the aqueous medium.

According to the present invention, at the completion of the fermentation period the pH of the broth, which is usually basic, is adjusted to acid, preferably about pH 5.0 and a filter aid is admixed in the broth. The whole broth is filtered through a cloth and a paper filter. The pH of the filtrate is adjusted between 6 to 8, preferably about pH 8, and the filtrate is applied on a column packed with a neutral adsorbing resin. The adsorbed product is eluted from the column with a solution of acetone and dilute hydrochloric acid. The pH of the eluate is adjusted to 5 and concentrated under vacuum to a small volume. The pH of the concentrated eluate is made acid, preferably about pH 2.5 and filtered. The pH of the filtrate is made basic, preferably about pH 8 and the filtrate is extracted with ethyl acetate. The ethyl acetate extracts are concentrated under vacuum at an internal temperature of less than 20° C. to the first appearance of a gelatinous precipitate. The gelatinous solid is stirred with ethyl ether and the resulting solid filtered off and dried. This solid is subjected to the process of fractional crystallization at controlled pH as set forth below.

This crude solid is dissolved in water at a pH of 2.5. An insoluble inorganic residue is filtered off and the filtrate decolorized with activated charcoal. The resulting solution is slowly neutralized to about pH 7 and the precipitated product filtered off. The product is again dissolved in pH 2.5 water, the solution decolorized and slowly neutralized to about pH 5. The solid is filtered off, washed with petroleum benzin, and methanol and dried. The solid obtained from the fractional crystallization and the solid obtained from the acid filtrates by further neutralizing to pH 7 and the solid obtained from evaporation of the methanol wash is further processed by fractional crystallization until all fractions are substantially pure.

EXAMPLE 1

Procedure for Production of 3,6-bis(5-chloro-2-piperidinyl)-2,5-piperazinedione by Fermentation of *Streptomyces griseoluteus* (NRRL 3412)

Stage 1 — A lyophilized culture of 3,6-bis(5-chloro-2-piperidinyl)-2,5-piperazinedione producing strain of *Streptomyces griseoluteus* (NRRL 3412) is suspended in 2 ml. of a medium consisting of Y.E.D (yeast extract dextrose) plus salts (F. B. Merck) and used to inoculate slants containing the same media plus 2% agar. The slants are then incubated at 28° C. for 5 days. Tap water is used throughout the fermentation work. Stage 2 — To a sporulated slant from Stage 1 is added 10 ml.

of a medium having a pH of 7 to 7.2 and consisting of:

|  | Percent* |
|---|---|
| Dextrose | 1 |
| N-Z amine E | 1 |
| NaCl | 0.5 |
| Meat extract | 0.3 |
| Distilled water, q.s., ad. | |

*percent of ingredients based on pre-inoculation volume.

The growth on the slant is scraped into the suspension and one ml. is used to inoculate a 250 ml. baffled Erlenmeyer flask containing 50 ml. of the same medium. The inoculated flask is then placed on a rotary shaker and incubated at 28° C. for 72 hours. The resulting vegetative growth is used immediately in Stage 3. Stage 3 — An inoculum of 10 ml. of the resulting vegetative growth from Stage 2 is used to inoculate a 2 l. baffled Erlenmeyer flask containing 500 ml. of sterilized medium of the same composition as shown above in Stage 2, and the inoculated flask is placed on a rotary shaker and incubated at 28° C. for 84 hours. Stage 4 — The fermentation broth resulting from Stage 3 is used to inoculate a 50-gallon stainless steel fermentor containing 160 l. of the medium of the same composition shown above in Stages 2 and 3. The inoculated medium is incubated at 28° C. with agitation at 150 r.p.m. while maintaining an air flow of 3 c.f.m. through the fermentation broth. During the 96 hour fermentation period, small amounts of an antifoam agent (Polyglycol 2,000) are added to control foaming.

Determinations are made periodically of pH, dextrose concentration and dry weight as follows:

| Age In Hours | pH | Dextrose mg./ml. | Dry weight gms./l. |
|---|---|---|---|
| 0 | 7.0 | 9.4 | 0.2 |
| 12 | 6.9 | 9.4 | 0.3 |
| 24 | 6.9 | 9.4 | 0.6 |
| 36 | 7.0 | 9.2 | 0.7 |
| 48 | 7.2 | 8.8 | 1.1 |
| 60 | 7.4 | 8.3 | 1.8 |
| 72 | 7.7 | 7.8 | 2.2 |
| 84 | 7.8 | 7.3 | 2.3 |
| 96 | 8.1 | 7.1 | 2.4 |

The resulting fermentation broth is used immediately in Stage 5. Stage 5 — 43 liters of the broth resulting from Stage 4 is used to inoculate a 200-gallon stainless steel fermentor containing 467 l. of the same medium as in Stages 2, 3 and 4. The inoculated medium is incubated at 28° C. with agitation at 130 r.p.m. while maintaining an air flow of 10 c.f.m. through the fermentation broth. During the 48 hour fermentation period, small amounts of an antifoam agent (Polyglycol 2,000) is added as needed to control foaming of the batch.

Determination is made periodically of pH dextrose concentration and dry weight as follows:

| Age In Hours | pH | Dextrose mg./ml. | Dry Weight gms./l. |
|---|---|---|---|
| 0 | 7.0 | 8.7 | 0 |
| 12 | 7.2 | 8.5 | 0.3 |
| 24 | 7.5 | 8.4 | 2.0 |
| 36 | 7.6 | 7.9 | 2.1 |
| 48 | 7.9 | 7.3 | 2.8 |

Stage 6 — 454 liters of the fermentation broth resulting from Stage 5 is used to inoculate a 1500-gallon stainless steel fermentor containing 4060 liters of medium having the following composition:

|  | G./l.* |
|---|---|
| Dextrose | 10.0 |
| Peptone | 5.0 |
| NaCl | 12.7 |
| Yeast extract | 3.0 |
| KCl | 0.72 |
| $FeSO_4(NH_4)_2SO_4 \cdot 6H_2O$ | 0.035 |
| $MgCl \cdot 6H_2O$ | 5.32 |
| $CaCl_2 \cdot 2H_2O$ | 0.728 |
| Distilled water, q.s., ad. | |
| pH 7.5 before sterilization | |

*All ingredients based on the pre-inoculation volume.

The batch is incubated at 28° C. for 120 hours with agitation at 0.0265 r.p.m./l. while maintaining an air flow of 0.143 c.f.m./l. through the broth. Addition of defoamer (Polyglycol 2000) is kept to a very minimum required to control foam out. The total used is 600 ml.

Determination is made periodically of pH, dextrose concentration dry weight and antibiotic activity:

| Age hrs. | pH | Dextrose mg/ml | Dry Weight gms/l. | Plate Activity Vibrio percolans ATCC 8461 mm. | Plate Activity Pseudomonas stutzerii ATCC 1160 mm. | *Tube Assay Pseudomonas stutzerii ATCC 11607 St. | 1–8 | 1–16 | 1–32 | 1–64 | 1–128 |
|---|---|---|---|---|---|---|---|---|---|---|---|
| 0 | 7.0 | 9.3 | 0.5 | | | | | | | | |
| 12 | 7.4 | 9.3 | 0.8 | | | | | | | | |
| 24 | 7.5 | 9.3 | 1.7 | | | | | | | | |
| 36 | 7.8 | 8.2 | 3.5 | | | | | | | | |
| 48 | 7.9 | 7.9 | 3.6 | | | | | | | | |
| 60 | 7.9 | 7.6 | 4.3 | | | | | | | | |
| 72 | 8.0 | 6.7 | 4.8 | 16 | 16 | + | + | + | ± | ± | ± |
| 84 | 8.1 | 5.9 | 4.8 | 18 | 18 | | | | | | |
| 96 | 8.1 | 4.7 | 5.1 | 20 | 20 | + | + | + | + | ± | ± |
| 108 | 8.1 | 3.7 | 5.5 | 20 | 21 | | | | | | |
| 120 | 8.1 | 3.2 | 5.0 | 20 | 21 | + | + | + | + | + | ± |

*Average standard for this assay equals a + at the 6.2 µg/ml level.

EXAMPLE 2

Isolation and Purification of 3,6-bis(5-chloro-2-piperidinyl)-2,5-piperazinedione from Fermentation Broth Stage 1 — Adsorption on Amberlite XAD-2.

At the completion of the fermentation period, the entire batch of fermentation broth obtained from Example 1, Stage 6, which totals 1200 gal. is transferred from the fermentors by air pressure into a brined (5°–10° C.) stainless steel (s.s.) tank. The pH is adjusted from about 8 to 5.0 with concentrated hydrochloric acid. Supercel (Johns Manville Highflo), 240 lb., a filter aid, is admixed with the broth, and the mixture is filtered through a 30 inch filter press set with filter cloth and Sharkskin filter paper. The clear, light brown filtrate is collected into two 800 gal. brined s.s. tanks, and the filter cake is washed with de-ionized water to bring the filtrate to the original broth volume. The pH of the combined filtrate and water wash is adjusted to 8 with 34% sodium hydroxide solution, and the alkaline broth is adsorbed at a rate of 5 gal./min, onto 95 gal. of regenerated, pretreated Amberlite XAD-2 resin. (A Rohm and Haas Co. tradename for neutral adsorbing resin.)

The resin is regenerated by first washing it free of eluant with 300 gal. of water. It is then removed to a s.s. column where it is washed downflow in the following sequence:

1. A solution of 408 gal. of methanol, 12 gal. of water and 66 l. of concentrated ammonium hydroxide.
2. Water to wash free of methanol and ammonia.
3. 420 gal. of acetone.
4. Water to wash free of acetone.

The regenerated resin is back washed with water to remove fines and to reclassify the bed.

The resin is packed in a 30 inch diameter Ceilcote Duracor 6000 plastic column, and occupies a height of 33 inches. After absorption, the broth is drained to bed level and a 200 gal, water wash is applied, again draining the last of the water wash to bed level. The spent broth and wash are discarded. The esin is next eluted with a solution of 50% acetone/50%-0.1N hydrochloric acid. The following column fractions are taken: a. 50 gal. forecut; b. 250 gal. rich or main cut; and c. 60 gal. tail cut. The main cut is received in a 250 gal. stainless steel (s.s.) kettle, and after adjusting the pH to 5.0 with 34% sodium hydroxide solution, it is concentrated. The concentration is carried out in a s.s. evaporator under vacuum (28 inches Hg) at 20° C. to a final volume of 10 gal. Free steam is used in the evaporator jacket to a volume of 25 gal. at which point the steam is replaced with hot water. The 10 gal. concentrate is transferred to a s.s. kettle, and the evaporator rinsed with 2 gal. of water. The pH of the combined concentrate and water wash is adjusted to 2.5 with concentrated hydrochloric acid, and the mixture is clarified in a Sharples Centrifuge (4 inch bowl). The clear supernatant is collected in a s.s. receiver, and the dark, slimy Sharples cake is discarded after washing it with 1 l. of water. The pH of the combined dark concentrate and wash is adjusted to 8 with sodium hydroxide solution, and extracted with 4 × 9 gal. of ethyl acetate in a 30 gal. glass lined extractor. Solids found in the organic layers or at the interface contain product. These interface solids amounting to 70 g. are filtered off on a large Buchner funnel fitted with Sharkskin filter paper and washed with ethyl acetate. They are held while drying under vacuum at room temperature and purified later with the "ethyl acetate solids." After each extraction, the pH of the aqueous phase drops a few tenths of a unit; it is readjusted to 8.0 ± 0.1 prior to the next extraction. The combined ethyl acetate extracts are concentrated under vacuum in a glass lined still at 25° to a volume of 10 gal.

The concentration of the ethyl acetate extract is completed in 12 l. flasks under vacuum (5–10 mm.) using a water bath at 40°–60° C. to give a gelatinous solid. Internal temperatures greater than 20° C. are avoided, especially towards the end of the concentration.

The above interface solids, amounting to 70 g. are combined with the gelatinous material resulting from the concentration of the extracts, and the mixture is stirred in 20 l. of ethyl ether. After sufficient washing, a solid (a) is obtained (throughout the remainder of the Example letters of the alphabet refer to Table I), which is filtered off, slurried with ether in a Waring Blendor, and finally washed thoroughly with petroleum benzin. The yield of crude tan material, dried at r.t./0.1 mm./$P_2O_5$/18 hrs., is 139 g. (a). Unless otherwise specified, all products are dried under these conditions. From this point on, the stepwise purification of 593A to final product is followed by tlc.

Stage 2 — Purification of 3,6-bis(5-Chloro-2-piperidinyl)-2,5-piperazinedione, Compound 593A Free Base by Fractional Crystallization at Controlled pH The following is a schematic presentation of the stepwise purification of Compound 593A, starting with the "ethyl acetate solids" of Stage 1.

TABLE I

"Ethyl Acetate Solids" - 1200 gal. Batch 139 g. (a) crude     540 g. (e) oil 60.55 (b) ca. 90% pure    plus    { 8.0 g. inorganic; 4.1 g. (c) MeOH Solids; 8.8 g. (d) pH 5–7 }

40.4 g. (i) at least 99% pure free base    plus    { 3.6 g. (f) 1st pH 5–7; 4.85 g. (g) 2nd pH 5–7; 3.52 g. (h) MeOH wash }

(c) + (d) + (f) + (g) + (h) = 24.6 g.

10.2 g. (j) at least 99% pure free base    plus    { 4.7 g. (l) 1st pH 5–7; 4.4 g. (m) 2nd pH 5–7; 1.5 g. (n) MeOH wash }

(l) + (m) + (n) = 10.6 g.

6.75 g. (k) at least 99% pure free base    plus    { 1.0 g. (o) 1st pH 5–7; 1.2 g. (p) 2nd pH 5–7; 0.8 g. (q) MeOH wash }

(i) + (j) + (k) = 57 g. free base

| HCl 57.0 g. (r) final product Compound 593A    plus    { 1.3 g. (s) from MeOH mother liquors; 0.5 g. (t) from MeOH wash }

Fraction (a) is further purified by fractional crystallization as follows. To a stirred suspension of the 139 g. (a) in 6950 ml. (50 ml./g.) of water (distilled water is used throughout this purification) is added slowly concentrated hydrochloric acid to pH 2.5. Insoluble particles are ground under dilute hydrochloric acid to insure solubilization of all product. A dark gray solid (8.0 g., mostly inorganic) is filtered off, and the brown filtrate is decolorized three times, using 14 g. of decolorizing charcoal each time. The resulting pale green solution is stirred and neutralized to pH 7 by the dropwise addition of 25% sodium hydroxide solution. The first persistent precipitation occurs at pH 4.4. The cream cake is filtered off, washed with 2 × 1 l. of water (all washings are carried out by stirring in a beaker for a few minutes), and the still moist cake resuspended in 3 l. of water. Solution is effected by the addition of concentrated hydrochloric acid to pH 2.5 previously, and the slightly hazy solution treated twice with 14.0 g. of decolorizing charcoal. After the second charcoal treatment, the solution is colorless. It is stirred and neutralized to pH 5 by the slow dropwise addition of a 5% sodium hydroxide solution over a period of 45 minutes. The first persistent precipitate forms at pH 4.0. The white cake is filtered off, washed with 2 × 1 l. of water, 2 × 500 ml. of methanol and 2 × 750 ml. of petroleum benzin, and dried; yield 60.5 g. (b). Concentrations of the methanol wash to dryness at 0.1 mm. in a water bath <25° C. gives 4.1 g. (c) of solid. The aqueous filtrate from the pH 5 fractionation and the water washes are combined, and the pH of the solution adjusted to 7 from which mixture 8.8 g. (d) is obtained after washing with water and drying.

The ether and petroleum benzin from the trituration of the "ethyl acetate solids" are concentrated to dryness. The residual, red viscous oil, 540 g. (e) is discarded. As indicated by tlc, it is a mixture of impurities containing only traces of 593A free base.

According to the tlc assays, the main product (b) at this stage is 90–95% pure, while the solids from the methanol wash (c) and the pH 5–7 fraction (d) are less pure. Fraction (b), 60.3 g. is suspended in 2.5 l. of water, and the mixture is treated through the steps of solubilization at pH 2.5, and treatment with 2 × 6.0 g. of decolorizing charcoal as described above. The volume of the colorless filtrate including washes is 3 l. Slow neutralization of the solution to pH 5 (first permanent precipitate at pH 3.6) with 5% sodium hydroxide solution gives a solid which is washed with 2 × 1 l. of water, plus 2 × 100 ml. of water used for transfer of the solid. The moist cake is resuspended in 2.5 l. of water and the above procedure repeated, including two additional washes each of 600 ml. of methanol and 600 ml. of petroleum benzin. The yield of dried purified 593A free base is 40.4 g. (i). The aqueous filtrate and wash from the first pH to 5 fractionation gives 3.6 g. (f) of pH 5–7 fraction; the corresponding filtrate and wash from the second pH to 5 fractionation gives 4.85 g. (g) of pH 5–7 fraction, while the methanol washes yield 3.52 g. (h). A combination of these less pure fractions (c), (d), (f), (g), (h), (24.6 g.) is suspended in 1.25 l. of water and treated through two pH 5 fractionations as just described; the yield of pure 593A pure base thus obtained is 10.2 g. (j). The first pH 5–7 fractionation gives 4.7 g. (l), the second pH 5–7 yields 4.4 g. (m); while the methanol washes give 1.54 g. (n). Applying the same two fractionation cycles to the combined impure fractions (l), (m) and (n) (10.6 g.), there is obtained an additional 6.75 g. (k) of Compound 593A free base whose purity is comparable to samples (i) and (j). All are at least 99% pure by tlc (essentially single spot).

In the last fractionation series, the first pH 5–7 cut amounts to 1.0 g. (o); the second pH 5–7 cut is 1.2 g. (p); and the methanol wash residue weighs 0.8 g. (q).

The three purified free base fractions, (i), (j), and (k), are combined and converted to the dihydrochloride salt under anhydrous conditions. The total, 57.0 g. (0.163 m.), is dissolved in 22.8 l. of methanol at room temperature with stirring. To the clear, filtered solution is added 23.8 g. (0.652 m.) of hydrogen chloride as a 20% solution in methanol. The well mixed solution is concentrated in a water bath at 50°–60°/5–10 mm. to a volume of 3 l. (50 ml./g. based on the original 57 g.).

During the concentration, the distillation of the methanolic hydrogen chloride is so rapid that the internal temperature maintains itself at 5°–10° C. After filtration of the cold mixture and removal of most of the solvent by suction, the cake is stirred in 2 l. of 2% methanolic hydrogen chloride for 45 min., filtered, and washed by displacement with 2 × 150 ml. of 2% methanolic hydrogen chloride. After a final wash by stirring is 1 l. of petroleum benzin for 5–10 min., the pure 593A is filtered off, dried first in air while pulverizing the larger lumps, and then dried at 40° C./0.1 mm./$P_2O_5$/18 hrs., yield 57.0 g. (r) (83%).

Calcd. for $C_{14}H_{22}Cl_2N_4O_2.2HCl$ (422.2) C, 39.83; H, 5.73; N, 13.27; Cl, 33.60 Found: C, 39.62; H, 5.92; N, 13.07; Cl, 33.81.

Concentration of the mother liquors yields 1.3 g. (s); the methanolic washes gives 0.5 g. (t).

The process set forth in this Example yields 57 g. of pure Compound 593A per 1200 gal. of fermentation broth.

What is claimed is:

1. A method of extracting and purifying the antibiotic 3,6-bis-(5-chloro-2-piperidinyl)-2,5-piperazinedione from a fermentation broth, which comprises:
    a. acidifying said fermentation broth to a pH of about 5, filtering the acidified broth to obtain a filtrate containing the antibiotic;
    b. adjusting the pH of the filtrate to between 5 and 8;
    c. contacting the filtrate with a surface active agent to adsorb the antibiotic and eluting the antibiotic with a combination of surface active agent and eluant selected from:
        i. activated charcoal eluted with dilute mineral acid;
        ii. sulfonated copolymer of styrene cross-linked with divinyl benzene eluted with 4-normal hydrochloric acid;
        iii. polystyrene quaternary ammonium anion exchange resin or hydrophobic non-ionic macroprorous copolymers of polystyrene cross-linked with divinyl benzene eluted with water, lower alkanols, water and loweralkanols, loweralkanols and chloroform, loweralkanones and water or loweralkanones and dilute mineral acid;
    d. adjusting the pH of the eluate to about 5 and concentrating,
    e. adjusting the pH of the concentrated eluate to about 8, extracting with a loweralkyl ester of a loweralkanoic acid, butanol, benzyl alcohol or chloroform and concentrating the organic solvent to dryness to obtain the antibiotic in solid form;
    f. dissolving the antibiotic in acidified water and adjusting the pH to near neutral with base, and collecting the crystallized antibiotic.

2. The method of claim 1 wherein in Step c. the filtrate is adsorbed on a neutral non-ionic macroporous copolymer of styrene cross-linked with divinyl benzene adsorbing resin and eluted with a solution of acetone and hydrochloric acid.

3. The method of claim 2 wherein in Step c. the filtrate is adsorbed on the surface active agent XAD-2 and eluted with a solution of 50% acetone and 50% 0.1 normal hydrochloric acid; in Step 3. the concentrated eluate is extracted with ethyl acetate; and in Step f. the solid antibiotic is dissolved in pH 2.5 water, adjusted to pH of about 7 by the addition of sodium hydroxide solution, filtering off the crystallized solid; redissolving the crystallized solid in pH 2.5 water, adjusting the pH to about 5 and collecting the crystallized antibiotic.

* * * * *